(12) United States Patent
Miura et al.

(10) Patent No.: US 7,037,727 B1
(45) Date of Patent: May 2, 2006

(54) APPARATUS FOR MEASURING A MEDICAL SUBSTANCE; A SENSOR FOR USE IN THE APPARATUS; AND A SENSING ELEMENT FOR USE IN THE SENSOR

(75) Inventors: Norio Miura, Fukuoka (JP); Noboru Yamazoe, Kasuga (JP); Taizo Uda, Miyoshi (JP)

(73) Assignee: DKK Corporation, Tokyo (JP)

( * ) Notice: Subject to any disclaimer, the term of this patent is extended or adjusted under 35 U.S.C. 154(b) by 970 days.

(21) Appl. No.: 08/985,007

(22) Filed: Dec. 4, 1997

(30) Foreign Application Priority Data

Dec. 5, 1996 (JP) ............................... H8-340481
Nov. 21, 1997 (JP) ............................... H9-337737

(51) Int. Cl.
*G01N 33/543* (2006.01)

(52) U.S. Cl. ..................... 436/518; 385/12; 385/129; 385/130; 422/55; 422/57; 422/82.05; 422/82.11; 435/287.1; 435/287.2; 435/288.7; 435/808; 436/164; 436/165; 436/172; 436/524; 436/525; 436/527; 436/805

(58) Field of Classification Search ............... 385/12, 385/129, 130; 422/55, 57, 82.05, 82.11; 435/287.1, 287.2, 288.7, 808; 436/164, 165, 436/172, 518, 524, 525, 527, 805
See application file for complete search history.

(56) References Cited

U.S. PATENT DOCUMENTS 4,810,658 A * 3/1989 Shanks et al. ............... 436/172
4,844,613 A * 7/1989 Batchelder et al. .......... 356/311
4,857,273 A * 8/1989 Stewart ........................ 422/55
4,997,278 A * 3/1991 Finlan et al. ................ 356/128

(Continued)

FOREIGN PATENT DOCUMENTS

JP 63-271162 11/1988
JP 7-111435 11/1995

OTHER PUBLICATIONS

"Optical Sensor Using Surface Plasmon Resonance Phenomenon", Measuring and Control, vol. 36, No. 4 pp. 275-265, Apr. 1997.

(Continued)

*Primary Examiner*—Christopher L. Chin
(74) *Attorney, Agent, or Firm*—Katten Muchin Zavis Rosenman

(57) ABSTRACT

An apparatus for measuring a medical substance where a prism having a high refractive index, a thin metal film formed on one of the surfaces of the prism, a light source for making a light incident upon the thin metal film, and a detector for detecting an incident angle of a light being made incident upon a film on which a plasmon resonance phenomenon is generated on the thin metal film are provided. The medical substance, i.e. antigen as an object to be measured, is fixed to the surface of the thin metal film, and the condition for generating the plasmon resonance phenomenon is varied when a mixture of antibody which is coupled with the medical substance in a specific manner and a sample is made contact with a surface of the thin metal film; and the amount of the medical substance can be detected by recognizing the change with a high sensitivity.

12 Claims, 12 Drawing Sheets

U.S. PATENT DOCUMENTS 5,047,213 A * 9/1991 Finlan et al. ............. 422/82.11
5,229,833 A * 7/1993 Stewart ....................... 356/364
5,491,556 A * 2/1996 Stewart et al. .............. 356/445

OTHER PUBLICATIONS

"The resonant mirror: a novel optical biosensor for direct sensing of biomolecular interactions part 1: Principle of operation and associated instrumentation" Biosensors & Bioelectronics 8 (1993), pp., 347-353.

"A fiber-optic chemical sensor based on surface plasmon resonance", Sensors and Actuators B. 12 (1993) pp. 213-220.

"Immunoassay of methamphetamine", The Chemical Society of Japan, 70th Spring Annuity Meeting 96.

* cited by examiner

APPARATUS FOR MEASURING A MEDICAL SUBSTANCE; A SENSOR FOR USE IN THE APPARATUS; AND A SENSING ELEMENT FOR USE IN THE SENSOR

BACKGROUND OF THE INVENTION

1) Field of the Invention

The present invention relates to an apparatus for measuring a medical substance where a resonance phenomenon with an evanescent wave, such as a surface plasmon resonance phenomenon, is used; a sensor for use in the apparatus; and a sensing element for use in the sensor. Particularly, the present invention can be preferably applied for measuring medical substances contained in body fluids, such as urine or blood, for example, organic medical substances, such as morphine, methamphetamine, cocaine and diacetylmorphine, which act as an antigen having a small molecular weight.

2) Prior Art

Many methods for detecting medical substances contained in body fluids such as urine or blood have been suggested. For instance, chromatography analysis, mass spectroscopy analysis, precipitation reaction analysis and spectrochemical analysis can be mentioned. However, according to these conventional methods, complicated pre-treatment process, for instance, extracting or refining, is required in order to adjust a sample liquid for use in detection. Furthermore, the analyzing sensitivity of these conventional methods is so low as not to be able to use practically.

On the other hand, nowadays, attention is being made to a new method for analyzing medical substances contained in body fluid where a resonance phenomenon with an evanescent wave is used, because according to the new method it can be expected to measure medical substances with a high level of sensitivity. The evanescent wave is a light wave which is exponentially attenuated in accordance with the distance from a boundary so that the light wave substantially has no energy, for example, like a light wave which is generated when light is totally reflected.

A well known resonance phenomenon with an evanescent wave is a surface plasmon resonance phenomenon which is generated when the wave number of evanescent waves becomes coincident with the wave number of the surface plasmon. When the surface plasmon resonance phenomenon is generated, a part of the energy of light is used to excite the surface plasmon, so that the generation of the surface plasmon resonance can be obtained as a reduction of the energy of the light. Since the condition for generating the surface plasmon resonance phenomenon, i.e. an incident angle or a wave number of the incident light, varies according to the condition of the substance which is made to contact with the sensing layer, information about the condition of the substance can be obtained by examining the condition for generating the surface plasmon resonance phenomenon.

For instance, when a thin metal film is formed on a surface of a prism and a light is made incident upon the prism to be reflected by the boundary surface of the prism and the thin metal film, the evanescent wave goes out of the prism and then propagates along the surface of the prism. If the metal film is sufficiently thin, the evanescent wave passes through the metal film. The wave number of the evanescent wave depends on the incident angle of the incident light. On the other hand, the surface plasmon is an elementary excitation of a surface plasma oscillation, which corresponds to the fact that the quantum, i.e. an energy, of the plasma oscillation localized on the surface is quantized. A metal can be considered as a solid-state plasma where free electrons are moving in the background of the fixed cations, and therefore a surface plasmon can be generated on the surface of the metal. The wave number of the surface plasmon depends upon a refractive index of the substance being made to contact with the thin metal film.

When the refractive index is varied by the fact that the condition of the substance being made to contact with the thin metal film is changed, the wave number of the surface plasmon is varied and then the wave number of the evanescent wave is also varied. That is to say, the wave number of the evanescent wave, at which the light intensity of the reflection light decreases, is varied. Since the wave number of the evanescent wave depends on the incident angle of the incident light, the incident angle, at which the light intensity of the reflection light decreases, i.e. a resonance angle, is changed. Therefore, the condition of the substance which is made to contact with the thin metal film, more concretely the refractive index of the substance, can be obtained by reading out the change of the incident angle, i.e. the resonance angle. It should be noted that the greater the refractive index of the substance being made to contact with the thin metal film, the larger the resonance angle, and generally, the heavier the molecular weight of the substance, the greater the refractive index.

A resonance phenomenon using a resonant mirror is also well known as another resonance phenomenon with an evanescent wave. The resonant mirror has a constitution such that a dielectric resonant layer, e.g. a layer made of Titania, having a thickness of 100 nm and a high refractive index is made to contact with a prism via a layer, i.e. a layer made of Silica, having a thickness of 1 μm and a low refractive index. The resonant mirror works in such a manner that when the layer having a low refractive index is sufficiently thin, a light (an evanescent wave) approaches to the dielectric layer having a high refractive index and then a resonance phenomenon is caused. When the wave number of the resonance mode of the layer having a high refractive index is coincident with the wave number of the incident light being made incident upon the prism with a certain incidence angle, the light may couple into the resonant layer efficiently, and then an evanescent light is generated on the sensing interface. The evanescent light can be detected as a change of phase which is caused in accordance with the change of the condition of the substance (more concretely, the change of the refractive index of the substance) being made to contact with the sensing interface. That is to say, when the resonant mirror is used, the refractive index of the substance which is made to contact with the layer having a high refractive index can be known by detecting the incident angle of the incident light at which the phase of the reflected light of the incident light is varied.

In this manner, the resonance phenomenon with the evanescent wave is caused depending upon the refractive index of the substance which is made to contact with the sensing interface. Then, it is tried to preliminarily fix an antibody to the resonance material, i.e. the thin metal film, and then to measure a medical substance which acts as an antigen coupled with the antibody fixed to the material in a specific manner. That is to say, when a sample liquid containing a medical substance is made to contact with the thin metal film, etc. on which the antibody is fixed, the medical substance contained in the sample is coupled with the antibody and then the refractive index is varied. Therefore, the amount of the medical substance contained in the sample liquid can be obtained by comparing the condition (the resonance angle, etc.), when the antibody is fixed to the thin metal film but the medical substance is not coupled with the antibody yet, with the condition (the resonance angle, etc.) after the medical substance is coupled with the antibody.

However, the medical substance contained in a body fluid, such as urine or blood, generally has only some hundreds molecular weight, which is quite small. Therefore, even if such a small molecular weight of substance is coupled with the antibody, a sufficient change of the refractive index cannot be obtained. It means the amount of change of the resonance angle is also very small. Thus, it is difficult to measure such an organic medical substance having a low molecular weight by using the surface plasmon resonance phenomenon in a direct manner.

In order to overcome this problem, a new method is suggested where a standard substance is prepared having a high molecular weight, such as protein, and is coupled with a medical substance to be detected in order to increase the molecular weight, and then the standard substance and the medical substance contained in the sample liquid to be measured are coupled with the antibody by competitive assay to improve the sensitivity. (Japan Chemical Association, 70th annually meeting in spring, "Measurement of methamphetamine using an immunological reaction", by Niimoto, et al).

SUMMARY OF THE INVENTION

The present invention has for its object to provide an apparatus for measuring a medical substance; a sensor for use in the apparatus; and a sensing element for use in the sensor; by which even a medical substance having a low molecular weight can be measured more easily with a high sensitivity using a resonance phenomenon with an evanescent wave, such as a surface plasmon resonance phenomenon.

In order to carry out the object mentioned above, the present inventors paid attentions to the fact that an antibody has a greater molecular weight than an antigen, and if it is arranged such that the antigen is preliminarily fixed to the resonance material whereby a resonance phenomenon can be generated in resonating with the evanescent wave and the antibody having a higher molecular weight is coupled therewith, a sufficient change of resonance condition, such as a resonance angle responding to the amount of the antibody coupled to the antigen preliminarily fixed to the resonance material, can be obtained. The inventors, then investigated the fact that the amount of the medical substance as an antigen can be indirectly measured from the amount of the change of the resonance condition, such as the resonance angle, which corresponds to the amount of the antibody coupled to the fixed antigen. More concretely, a known amount of antibody is mixed with and reacted to a sample liquid, and then the mixed liquid is made to contact with the resonance material, such as a thin metal film, etc. In this manner, the residue of antibody, which has not been reacted with the antigen in the sample liquid, is coupled to the antigen which has been preliminarily fixed to the resonance material. Then the coupled antibody can be measured in responding to the change of the resonance condition.

An apparatus for measuring a medical substance according to the first invention of the present application comprises a sensor having a resonance material, where a medical substance, i.e. an antigen, to be measured is fixed to the resonance material where a resonance phenomenon can be caused to resonate with an evanescent wave; and a detecting means for detecting a condition for generating said resonance phenomenon, which is sensed by said sensor.

Here, the concept of the resonance phenomenon in resonating with the evanescent wave includes, but is not limited to, a surface plasmon resonance phenomenon and a resonance phenomenon using a resonant mirror as mentioned above. Therefore, a thin metal film, a diffraction grating, or a layer made of Titania, etc. is preferably used as the resonance material as occasion demands. Further, the generating condition of the resonance phenomenon is detected as a resonance angle, a wave length of the reflected light, or a phase of the reflected light.

An apparatus for measuring a medical substance according to the first invention of the present application has another aspect in that the apparatus further comprises a calculating means for recognizing an amount of the medical substance contained in a sample liquid from a change of said generating condition of the resonance phenomenon which is occurred when a mixture of an antibody which is coupled with said medical substance in a specific manner and said sample liquid is made to contact with a surface of said sensor to which said medical substance has been fixed.

A sensor for detecting a medical substance according to the second invention of the present application, which is for use in the apparatus according to the first invention, is characterized in that a medical substance, i.e. an antigen, to be measured is fixed to a resonance material where a resonance phenomenon can be generated in resonating with an evanescent wave.

An apparatus for measuring a medical substance according to the third invention of the present application comprises a sensor having a resonance material where a medical substance, i.e. an antigen, to be measured, is fixed to the resonance material where a resonance phenomenon can be generated in resonating with an evanescent wave and a detecting means for detecting a condition for generating a surface plasmon resonance phenomenon which is sensed by said sensor.

In the apparatus according to the third invention, a surface plasmon resonance phenomenon is used as the resonance phenomenon in resonating to the evanescent wave.

An apparatus for measuring a medical substance according to the third invention of the present application has another aspect in that the apparatus comprises a calculating means for recognizing an amount of the medical substance contained in a sample liquid from a change of said generating condition of the surface plasmon resonance phenomenon which is generated when a mixture of an antibody which is coupled with said medical substance in a specific manner and said sample liquid is made to contact with a surface of said sensor to which said medical substance has been fixed.

A sensor for detecting a medical substance according to the fourth invention of the present application, which is for use in the apparatus according to the third invention, is characterized in that a medical substance, i.e. an antigen, to be measured is fixed to a resonance material by which a surface plasmon resonance phenomenon can be generated in resonating with an evanescent wave.

An apparatus for measuring a medical substance according to the fifth invention of the present application comprises a prism having a high refractive index, a thin metal film formed on one of the surfaces of said prism directly or indirectly, a light source for supplying an incident light on said thin metal film via said prism, a detecting means for detecting an incident angle of said incident light at which a surface plasmon resonance phenomenon is generated on said thin metal film via said prism, wherein a medical substance, i.e. antigen as an object to be measured is fixed on a surface of said thin metal film which is located on an opposite side of the surface where said prism is provided.

In the apparatus according to the fifth invention, the surface plasmon resonance phenomenon is used; further the thin metal film is used as a resonance material, which is formed on one of the surfaces of the prism directly or indirectly. It should be noted that to form the metal film on the surface of the prism indirectly means to prepare a thin metal film independently, for instance, on a base plate, and to provide the base plate with the film on the surface of the prism.

An apparatus for measuring a medical substance according to the fifth invention of the present application has another aspect in that the apparatus further comprises a calculating means; wherein a medical substance, i.e. antigen as an object to be measured, is fixed on a surface of said thin metal film which is located on an opposite side of the surface where said prism is provided; and wherein an amount of the medical substance contained in a sample liquid is recognized by said calculating means from a change of said incident angle of the incident light when a mixture of an antibody which is coupled with said medical substance in a specific manner and said sample liquid is made contact with the surface of said metal thin layer where said medical substance has been fixed.

A sensor according to the sixth invention of the present application, which is for use in the apparatus according to the fifth invention, comprises a prism having a high refractive index, a thin metal film formed on one of the surfaces of said prism directly or indirectly; wherein a medical substance, i.e. antigen as an object to be measured is fixed to another surface of said thin metal film which is located on an opposite side of the surface where said prism is provided.

A sensing element according to the seventh invention of the present application comprises a base plate which is arranged to be able to be mounted on one of the surfaces of a prism having a high refractive index, and a thin metal film formed on one of the surfaces of said base plate; wherein a medical substance, i.e. antigen as an object to be measured, is fixed on a surface of said thin metal film which is located on an opposite side of the surface where said base plate is provided.

The sensing element according to the seventh invention is used under the condition that the element is mounted on the prism having a high refractive index for use in measuring apparatuses where the surface plasmon resonance phenomenon is used to detect the medical substance. According to the seventh invention, in order to make it widely used, it is preferred to provide a base plate, e.g. a glass plate, on which a thin metal film is formed, on the surface of the prism.

DETAILED EXPLANATION OF THE PREFERRED EMBODIMENTS

Figure 1:
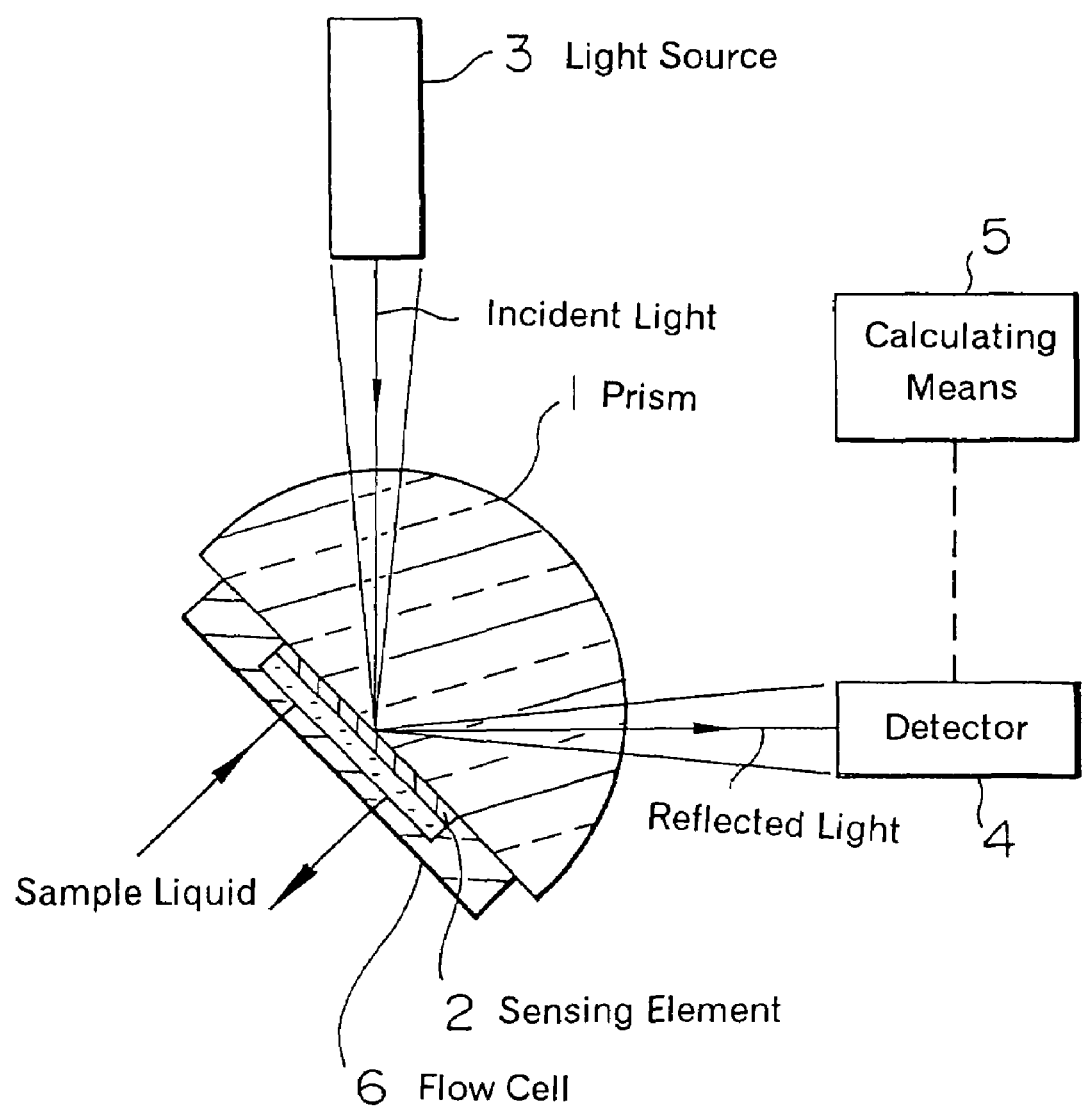
FIG. 1 is a schematic view showing a construction of an apparatus for measuring a medical substance according to the invention.

The preferred embodiments of the present invention will be explained below. It should be noted that the medical substance, i.e. an antigen as an object to be detected, is not limited in the present invention, however, the present invention can be preferably applied to detect a medical substance having a low molecular weight, for instance, an antihypnotic, such as methamphetamine (molecular weight: 149.24), amphetamine (molecular weight: 135.21); a narcotic, such as morphine (molecular weight: 285.34), diacetylmorphine (heroin) (molecular weight: 369.42), codeine (molecular weight: 299.37), cocaine (molecular weight: 303.36), mesadon (molecular weight: 309.45), lysergic acid diethylamide (LSD) (molecular weight: 323.44); psychotropic medicines, such as phenobarbital (molecular weight: 232.24), diazepam (molecular weight: 284.74), nitrazepam (molecular weight: 281.27); and hemp, such as tetrahydrocannabinol (molecular weight: 314.47). The molecular weights of these medical substances are in a range between 100 to 400, more concretely 130 to 330. Such medical substances having low molecular weights could not be detected by conventional apparatuses where the surface plasmon resonance phenomenon, etc. are used, because their molecular weight is so low that the change of the refractive index of sensing layer on the thin metal film is not effectively occurred. Therefore, the measurement value in a conventional apparatus could not be evaluated in a clear condition.

As an antibody, which recognizes a medical substance (or an epitope of the medical substance) and couples to the substance, i.e. an antigen as an object to be measured, in a specific manner, a monoclonal antibody or a polyclonal antibody can be used without any limitation. The monoclonal antibody can be easily produced in accordance with the Kohler•Milstein method. Generally, antibody forming cell coming from Mammalian spleen cells, such as mouse cells, which are rendered immune by antigen and Myeloma cell of Mammalia, such as a mouse, are fused into one to obtain a hybridoma for producing an antibody; the thus obtained hybridoma is subjected to a screening with a selective medium to obtain a desired hybridoma; then the thus obtained desired hybridoma is cultivated to produce the monoclonal antibody. On the other hand, the monoclonal antibody is available by giving a hybridoma in a cavity of Mammalia, such as a mouse, and then generating monoclonal antibody from its abdominal dropsy.

According to the invention, a medical substance such as an antigen generally has a low molecular weight. Therefore, the antibody for a medical substance can be produced in such a manner that bovine serum albumin (BSA) or human serum albumin, etc. is coupled to the medical substance as a carrier to give an immunogen thereto, and is then cultivated.

A polyclonal antibody can be obtained in such a manner that after the carrier is added to the medical substance, the substance with the carrier is given into the cavity or under the skin of Mammalia, such as a mouse, and then obtaining a serum from the Mammalia and then refined.

FIG. 1 is a schematic view showing a construction of an example of the apparatus for measuring a medical substance according to the present invention where a surface plasmon resonance phenomenon is used to detect the objected medical substance.

The apparatus shown in FIG. 1 has so-called Kretschmann configuration, which comprises a prism 1 having a high refractive index, a sensing element 2 being mounted on one of the surfaces of said prism 1 and having a thin metal film formed on an opposite side of the surface where the prism 1 is provided, a light source 3 from which a light is emitted and the light is made incident upon said thin metal film 2 formed on said sensing element 2 through said prism 1, a detector 4 for receiving a reflected light on said thin metal film and detecting an incident angle of an incident light at which a surface plasmon resonance phenomenon is generated, a calculating device 5 for receiving a signal being sent from said detector 4 and for recognizing the amount of the medical substance contained in a sample, and a flow cell 6 which works as a field where the sample is made to contact with the metal film.

Any prism member having a high refractive index can be used for the prism 1 without any limitation. For instance, the BK7 (($n_d$=1.5163), SFL6 ($n_d$=1.80518) etc. can be preferably used for the prism material. The material is not limited to a glass, so that the other material, such as a plastic, can be used. Furthermore, the shape of the prism 1 is not limited, so that the prism having a semi-spherical shape, a triangle shape, etc. can be preferably used.

The sensing element 2 comprises a base plate made of a thin film made of glass or plastic, so-called a cover glass; and a thin metal film formed on one of the surfaces of the base plate. Any metal can be used as long as the metal can be formed on the base plate as a thin film. For instance, Platinum, Gold, Silver, Copper, Nickel, Iron, Aluminum, and Stainless can be preferably used; particularly, a thin metal film made of Gold is preferred. The preferred thickness of the metal film is 25 to 90 nm, more preferably, 40 to 60 nm. The metal film can be formed on the surface of the base plate by vacuum evaporation, coating, etc.

The sensing element 2 is mounted on the prism 1 so as to put the surface where the thin metal film is formed outside. The method for mounting the element on the prism 1 is not limited, so that many sorts of mounting method can be applied, for instance, a method using a matching oil with the aid of surface tension, adhering, or pressurizing the base plate with the aid of an adapter.

On the sensing element 2, the medical substance which is an antigen as an object to be measured is fixed to the thin metal film which is located on the opposite side of the base plate. In order to fix the medical substance on the thin metal film, there are considered the method for physically absorbing the antigen on which protein, etc. has been coupled, the method for chemically coupling the antigen on the surface of the thin metal film after a functional group having an affinity to the metal surface, such as thiol group or disulfide group, has been coupling to the antigen.

As the light source 3, any kind of light source having a wavelength 200 to 1300 nm, more preferably, 400 to 800 nm can be used. For instance, a light emitting diode which emits a light having a wavelength of 650 to 800 nm can be preferably used.

As the detector 4, for instance, a photodiode, a linear array, or a CCD camera, can be preferably used.

The calculating device 5 is provided for recognizing the amount of the medical substance contained in the sample on the basis of information obtained from the detector 4 about the comparison result that the resonance angle when the mixture liquid, where the antibody which is coupled to the medical substance in a specific manner and a sample liquid are mixed at a given ratio, is made contact with the surface of the thin metal film on which the medical substance has been fixed, is compared to the resonance angle before the mixture liquid is made contact with the surface of the thin metal film. It should be noted the concept of the recognition here includes not only to obtain a concrete value of the concentration of the medical substance contained in the sample but also to make a judgement by selection from two possibilities of if the concentration of the medical substance contained in the sample is beyond some standard value or not.

The flow cell 6 is a container for containing the sample liquid, inside of which the surface of the metal thin layer where the antigen is fixed is exposed. In the flow cell 6, there are provided an inlet and an outlet, so that the sample liquid is circulated there by a pump (not shown) to be made to contact with the metal thin layer.

According to the first embodiment, the carrier is passed through the flow cell 6, first, then the incident light emitted from the light source 3 is made incident upon the metal thin layer of the sensing element 2 through the prism 1, and then an incident angle (a resonance angle) at which the reflecting intensity of the reflected light becomes the minimum is detected as "a first resonance angle (1)".

Next, a mixture liquid of the antibody and the sample liquid which have been reacted together, is passed through the flow cell 6. The mixture liquid is prepared in such a manner that a certain amount of antibody which is coupled to the medical substance, which is an antigen as the object to be measured, in a specific manner is prepared, and the thus prepared antibody is mixed with the sample liquid to generate antigen-antibody reaction.

The resonance angle is then monitored after the mixture liquid is introduced into the flow cell 6, and the resonance angle is detected as "a second resonance angle (2)" when the monitored resonance angle becomes constant, assuming that the antigen-antibody reaction of the antibody left in the mixture liquid and the medical substance fixed on the thin metal film has been finished at that time.

The "second resonance angle (2)" should be greater than the "first resonance angle (1)" in response to the amount of antibody which had been coupled to the medical substance fixed on the thin metal film. That is to say, when the amount of the medical substance contained in the sample is small, the resonance angle largely varies, because a great amount of antibody is left in the sample, while, when the amount of the medical substance contained in the sample is great, the resonance angle does not vary so much, because the amount of the antibody left in the sample is small. Therefore, by preliminarily preparing an inspection line using a standard sample liquid which contains a medical substance having a known concentration, it is able to recognize the concentration of the medical substance contained in the sample in accordance with the amount of the change of the resonance angle which is detected by the detector 4.

It may be possible to introduce the liquid mixture into the flow cell 6 before the antigen-antibody reaction of the antibody and the antigen contained in the sample has not been completed. In this case, the left of the antibody is coupled to the medical substance contained in the sample liquid and to the medical substance fixed on the metal thin layer in a competitive manner.

It is preferred to conduct the antigen-antibody reaction mentioned above at a temperature of 5 to 45° C., more preferably 20 to 30° C. Further, in case more high measurement accuracy is required, it is preferred to make the temperature constant within the preferred range.

It should be noted that the sensor is reusable. In order to reuse it, an acid or alkali washing liquid should be introduced into the flow cell 6 so that the antibody coupled to the thin metal film is dissociated therefrom.

In the apparatus shown in FIG. 1, the sensor is constituted of the sensing element and the prism, and the thin metal film is formed on the prism via a thin film base plate. However, it may be possible to deposit the thin metal film on the prism directly and then fix the medical substance on the film to complete the sensor.

Furthermore, it may be possible to use a batch type cell instead of the flow cell 6. In this case, the sensor should be formed under the batch type cell so as to expose the thin metal film on the bottom surface of the cell. Moreover, the measurement apparatus having no cell can be considered where the sensor should be immersed into a container in which the sample liquid is contained.

The condition for generating the resonance phenomenon can be detected by measuring the light intensity of the reflected light of the incident light at a certain incident angle, beside of detecting the resonance angle as shown.

In FIG. 1, the surface plasmon measurement apparatus arranged as the Kretschmann configuration is shown, however, in addition to this, many other types of apparatus, such as the apparatus using Otto's optical configuration, the apparatus using diffraction grating, or the apparatus using an optical fiber can be applied measurement apparatus using the surface plasmon.

According to the Otto's optical configuration, the prism and the sensor according to the fourth invention of the present application are arranged, where a sample liquid to be detected is placed therebetween. In this case, the condition for generating the resonance phenomenon is detected by the resonance angle, or the reflection light intensity at a certain incident light angle.

In the case of the apparatus using a diffracting grating, the medical substance should be fixed on the surface of the diffracting grating to complete the sensor according to fourth invention of the present application. In this case, the condition for generating the resonance phenomenon is also detected by the resonance angle, or the reflection light intensity at a certain incident light angle. Further, the condition for generating the resonance phenomenon can also be obtained by obtaining a spectrum of a reflection light which is obtained from a white light and then detecting an attenuating wave length which is attenuated by a resonance caused with the reflected light.

Further, in the case of the apparatus using the optical fiber, a thin metal film is coated on the surface of the core of the optical fiber and the medical substance is fixed on the metal film to complete the sensor according to the fourth invention of the present application. In this case, the condition for generating the resonance phenomenon can be also obtained by obtaining a spectrum of a reflected light which is obtained from a white light and then detecting an attenuating wave length which is attenuated by a resonance caused with the reflected light.

Furthermore, the present invention can be applied on the apparatus using a resonant mirror. In this case, the medical substance is fixed to a dielectric layer made of Titania, for example, having a thickness of about 100 nm to constitute a sensor according to the second invention of the present application; and the condition for generating the resonance phenomenon can be obtained by detecting the incident angle at which the phase of the reflection light is changed.

It should be noted that the calculating means is not an elemental requirement in the apparatus according to the present invention. That is to say, even in the apparatus having no calculating means, it is possible to recognize the amount of the medical substance contained in the sample by using an eternal recorder or a personal computer to which the signal detected in the detector 4 is supplied.

The present invention will be explained in the following embodiments 1 and 2 in a more detail manner, however, it should be noted that the present invention is not limited by these embodiments. In the first embodiment, morphine contained in a sample is measured as the medical substance, and in the second embodiment methamphetamine is detected.

(1) Embodiment 1

Explanation of the Measurement Apparatus

In the first embodiment, the flow cell type measurement apparatus, SPR-20 manufactured by DKK is used. The basic construction of the apparatus is as shown in FIG. 1. In this apparatus, the sample liquid is circulated through the flow cell 6, so that the sample can be reacted with the antibody which has been coupled to the metal thin layer of the sensor for a sufficient time. A light emitting diode is used as the light source 3 which has a wave length of 680 nm; a CCD camera is used as the detector 4. The material of the prism is BK7; and the sensing element 2, which will be explained in detail below, is mounted on a flat surface of the prism 1 with the aid of a matching oil.

Preparation of the Sensing Element

The sensing element is completed in such a manner that a thin Gold film is formed on a cover glass (manufactured by Matsunami Glass Co., Ltd.) by a vapor evaporation; then morphine is fixed to the surface of the film.

① Synthesis of Normorphine

Demethylation of morphine was conducted in accordance with the method by Brine et al. as in the following.

After melting 3.82 g of morphine in 190 ml of Chloroform, 20.9 g of methylchloroformate and 16.0 g of sodium hydrogencarbonate are added; then the thus obtained mixture is refluxed for 8 hours. Non-organic material is filtered from the reacted material; the filtered material is subjected to a dehydration with the aid of anhydrous sodium sulfate; and a solvent medium is evaporated under a reduced pressure to obtain a residue thereof having a light yellow color and a viscosity. Into the thus obtained residue, 11.4 ml of 97% hydrazine hydrate is added, and then 15.2 ml of 64% hydrazine hydrate is further added; then the residue with the hydrazine hydrate is refluxed for 12 hours to deposit crystal. The thus deposited crystal is washed with water, acetone and chloroform to obtain 2.81 g of normorphine. Whether the thus obtained substance is a desired normorphine is checked by a nuclear magnetic resonance (NMR) method.

② Synthesis of N-(4-phthalimidebutyl) Normorphine

After melting 2.81 g of normorphine in 64 ml of dimethylholmamide, 4.39 g of N-(4-bromobutyl) phthalimide and 1.31 g of sodium hydrogencarbonate are added; and then is refluxed for 2 hours. After extracting a material from the reacted material with the aid of ethyl acetate, the extracted material is washed by saturated salted water; subjected to a dehydration with the aid of anhydrous sodium sulfate; a solvent medium is evaporated under a reduced pressure to obtain a residue having a black color and a viscosity. The thus obtained residue is refined by silica gel column (Wakogel C-200, 500 ml, developing solvent ethyl acetate→ ethyl acetate methanol=9:1). The fraction which shows only the spot of $R_f$=0.60 is dispensed by TLC (developing solvent ethyl acetate:methanol=5:1); then the solvent is removed under a reduced pressure to obtain 4.04 g of the objected material. Whether the thus obtained material is a desired N-(4-phthalimidebutyl) Normorphine is checked by a mass spectroscopy(MS).

③ Synthesis of N-(4-aminobutyl) Normorphine

Hydrazinolusis of N-(4-phthalimidebutyl) normorphine was conducted as in the following, where allyl alcohol is added in the reaction system in order to reduce a side reaction, referring the method by Rice et al.

Into 944 mg of N-(4-phthalimidebutyl) normorphine, 2.2 ml of allyl alcohol and 7.9 ml of 90% hydrazine hydrate are added; then is refluxed for one hour in a nitrogen atmosphere. The solvent is evaporated from the reacted material under a reduced pressure; and the thus obtained residue is refined by silica gel (Wakogel C-200) column (developing solvent chloroform:methanol:water:=10:10:1) The fraction which shows only the spot of $R_f$=0.25 is dispensed by TLC (developing solvent chloroform:methanol:water:=10:10:1); then the solvent is removed under a reduced pressure to obtain 618 mg of the objected material. Whether the thus obtained material is a desired N-(4-aminobutyl) normorphine is checked by a mass spectroscopy (MS).

④ Synthesis of Conjugate (MO-BSA) of N-(4-aminobutyl) Normorphine and Bovine Serum Albumin (BSA)

Into 0.3 ml of dimethylformamide, is melted 15 mg of N-(4-aminobutyl) normorphine; then the thus obtained material is further mixed with BSA solution (10 mg/1.5 ml). Into the mixed material, 0.5 ml of 10% solution of 1-ethyle-3-(3-dimethylaminopropyl) carbodiimide hydrochloric acid salt (EDC) is added; the pH thereof is adjusted to 5.5: and then stirred for 16 hours at a room temperature. The thus obtained material is subjected to a dialysis for super pure water, and then frozen and dried up to obtain 10 mg of synthesized material of N-(4-aminobutyl) normorphine and bovine serum albumin (MO-BSA: 10 mg).

⑤ Fixing the MO-BSA to the Thin Metal Film

Into the flow cell 6, circulated MO-BSA having a concentration of 100 ppm at a room temperature until the resonance angle becomes constant, i.e. for 3 to 5 minutes, to adhere to the MO-BSA on the thin metal film. Then, MO-BSA having a concentration of 1000 ppm is circulated into the flow cell until the resonance angle becomes constant, i.e. for 3 to 5 minutes, under a room temperature to conduct a blocking so that the MO-BSA is not physically adsorbed on the film any more.

Relation Between the Concentration of Antibody and the Amount of the Change of the Resonance Angle After completing to make the sensing element, a solution of monochronal antibody of morphine is introduced in the flow cell 6 and then circulated at a room temperature to study a relation between the concentration of antibody and the amount of change of the resonance angle.

Raw liquid (non-diluted) material of the antibody having a concentration of 1700 ppm is obtained in accordance with the above mentioned Kohler•Milstein method. The raw material is dissolved into PBS (16.2 mM of disodium hydrogen phosphate, 3.8M of disodium hydrogen phosphate, 100 mM of sodium chloride, 0.1% of sodium azide) to adjust five antibody solutions each having a different concentration in a range of 1 to 20 ppm.

Figure 2:
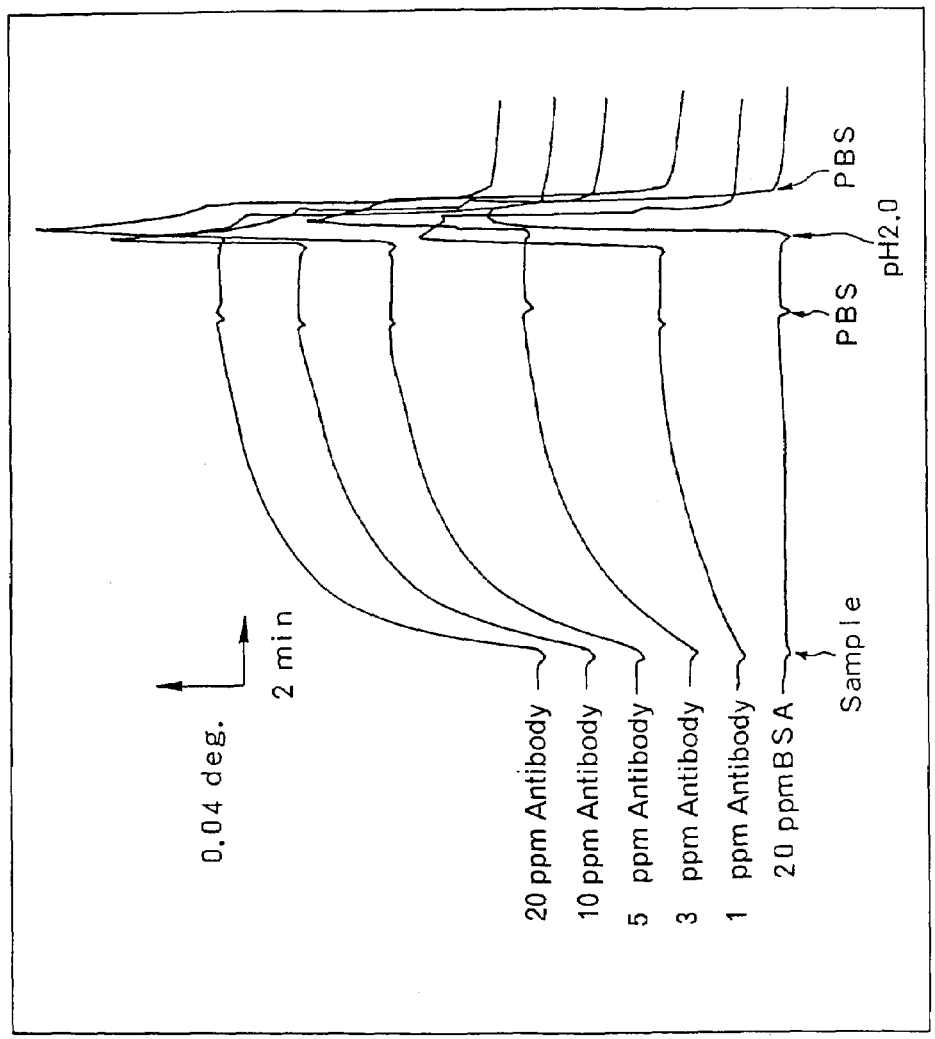
FIG. 2 is a graph depicting response curves of the resonance angles when solutions containing antibodies of morphine with different concentrations are introduced into the apparatus.
Figure 3:
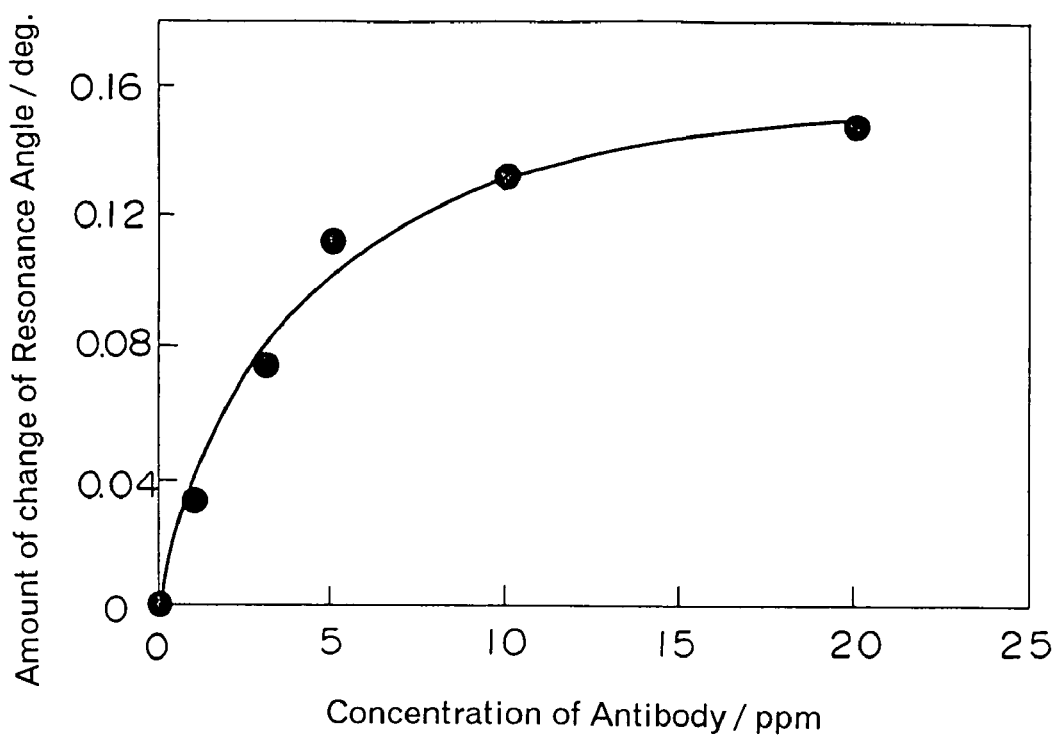
FIG. 3 is a graph illustrating a dependency of the response upon the concentration of the morphine when solutions containing antibodies of morphine with different concentrations are introduced into the apparatus.

FIG. 2 is a graph showing responding curves when each of the antibody solutions and BSA having a concentration of 20 ppm are mixed and then introduced in the flow cell 6. In FIG. 2, time is taken on a horizontal axis and the resonance angle is on a vertical axis, and the mark "sample" indicated by an arrow shows a time when each antibody solution or the BSA (sample) starts to be introduced in the flow cell 6. Further, FIG. 3 is a graph illustrating a dependency to the concentration of antibody in the response of the resonance angle, where the amount of the change of the resonance angle is taken on the vertical axis and the concentration of the antibody is on the horizontal angle. In FIG. 3, differences between the first resonance angle (1), which is obtained before the sample is introduced in the flow cell 6 and the second resonance angle (2) which is obtained after the antigen-antibody reaction has been finished and the response of the resonance angle has been stabilized are plotted.

As clear from FIG. 3, it is recognized that the resonance angle changes sufficiently in accordance with the change of the concentration of the antibody to be introduced into the flow cell. Further, it can be considered that the effect of the non-specific physical absorption of the antibody is very small because the resonance angle does not change at all when 20 ppm of BSA is introduced into the flow cell 6.

Relation Between the Concentration of Morphine and the Amount of the Change of the Resonance Angle Next, mixtures which are obtained by preliminarily reacting a certain amount of antibody having a concentration of 5 ppm and morphine (MO) are introduced into the flow cell 6 and circulated at a room temperature to study the relation between the concentration of morphine and the amount of change of the resonance angle.

Mixtures containing the antibody having a concentration of 5 ppm and morphine having a different concentrations in a range of 0.1 to 100 ppm were prepared in such a manner that that 3 µl of the raw liquid material of antibody having a concentration of 1700 ppm mentioned above and 1 ml of mixtures of morphine and PBS each having a different concentration of morphine are mixed together and reacted for about 5 minutes at a room temperature.

Figure 4:
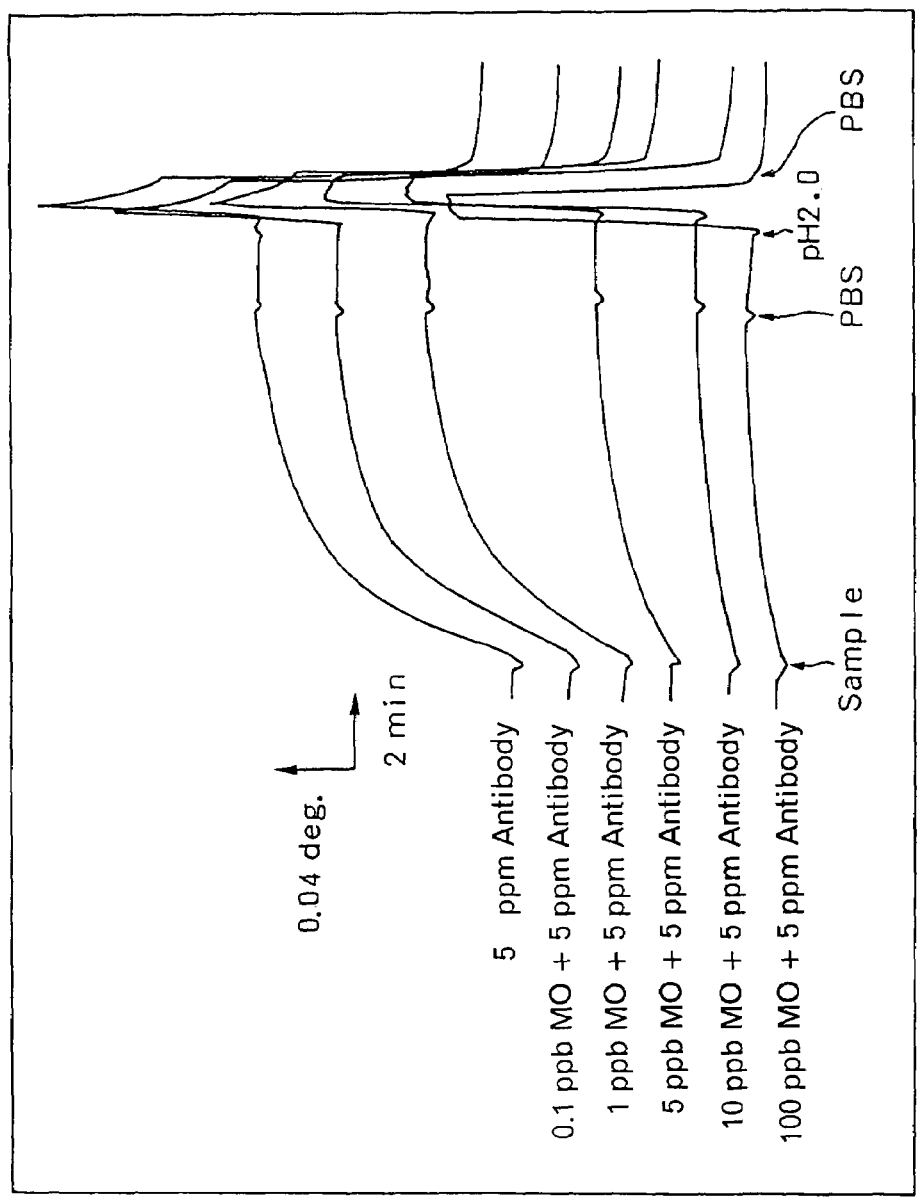
FIG. 4 is graph representing response curves of the resonance angles when mixtures each having antibody with a constant concentration of 5 ppm and morphine with different concentrations are introduced into the apparatus.
Figure 5:
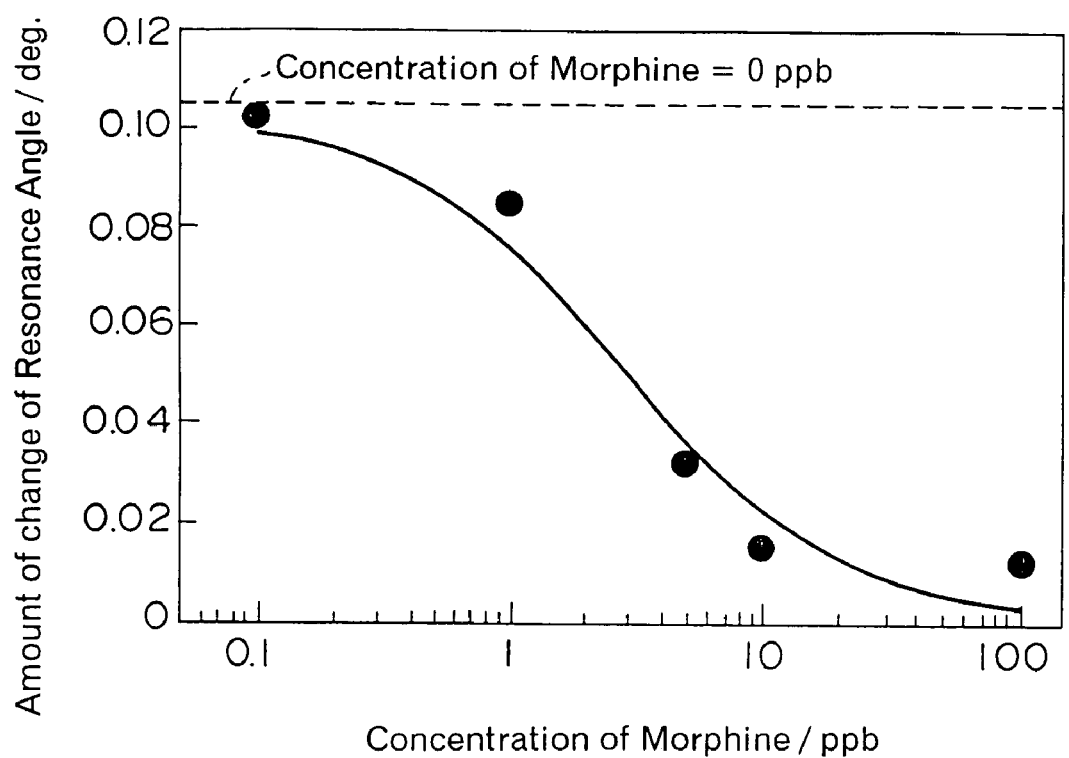
FIG. 5 is a graph showing a dependency response upon the concentration of morphine when mixtures each having antibody with a constant concentration of 5 ppm and morphine with different concentrations are introduced into the apparatus.

FIG. 4 is a graph depicting response curves when each mixture and 1 ml of the antibody solvent including no morphine are introduced in the flow cell. In FIG. 4, time is taken on the horizontal axis and the resonance angle is taken on the vertical axis; and the mark "sample" indicated by an arrow shows a time when each mixture and the solvent including no morphine start to be introduced into the cell. Further, FIG. 5 is a graph illustrating a dependency to the concentration of morphine in the response of the resonance angle, where the amount of the change of the resonance angle is taken on the vertical axis and the concentration of the antibody is on the horizontal axis. In FIG. 5, differences between the first resonance angles (1) before the samples are introduced and the second resonance angles (2) after the antigen-antibody reaction has been finished and the response has been stabilized are plotted.

It is recognized that a sufficient change of the resonance angle can be obtained in accordance with the concentration of the morphine contained in the mixture which is introduced in the flow cell.

Influence by the Other Composition Contained in Urine

It is considered that composition contained in urine gives a great influence to the sensitivity or specificity of immunological reaction. Then urine diluted to 10 to 100 times by PBS are prepared as buffer liquid; and antibody solutions having a concentration of 5 ppm with different concentrations of urine are introduced into the flow cell and circulated at a room temperature to study the relation between the concentration of the urine and the amount of change of the resonance angle.

Five antibody solutions having a concentration of 5 ppm using the urine diluted by PBS in a range of 10 to 100 times as the buffer solution were obtained by mixing 3 µl of the raw liquid material of antibody with a concentration of 1700 ppm to the buffer solution, i.e. urine diluted by PBS with a certain ratio, so as to have 1 ml of samples each having a different concentration of urine.

Figure 6:
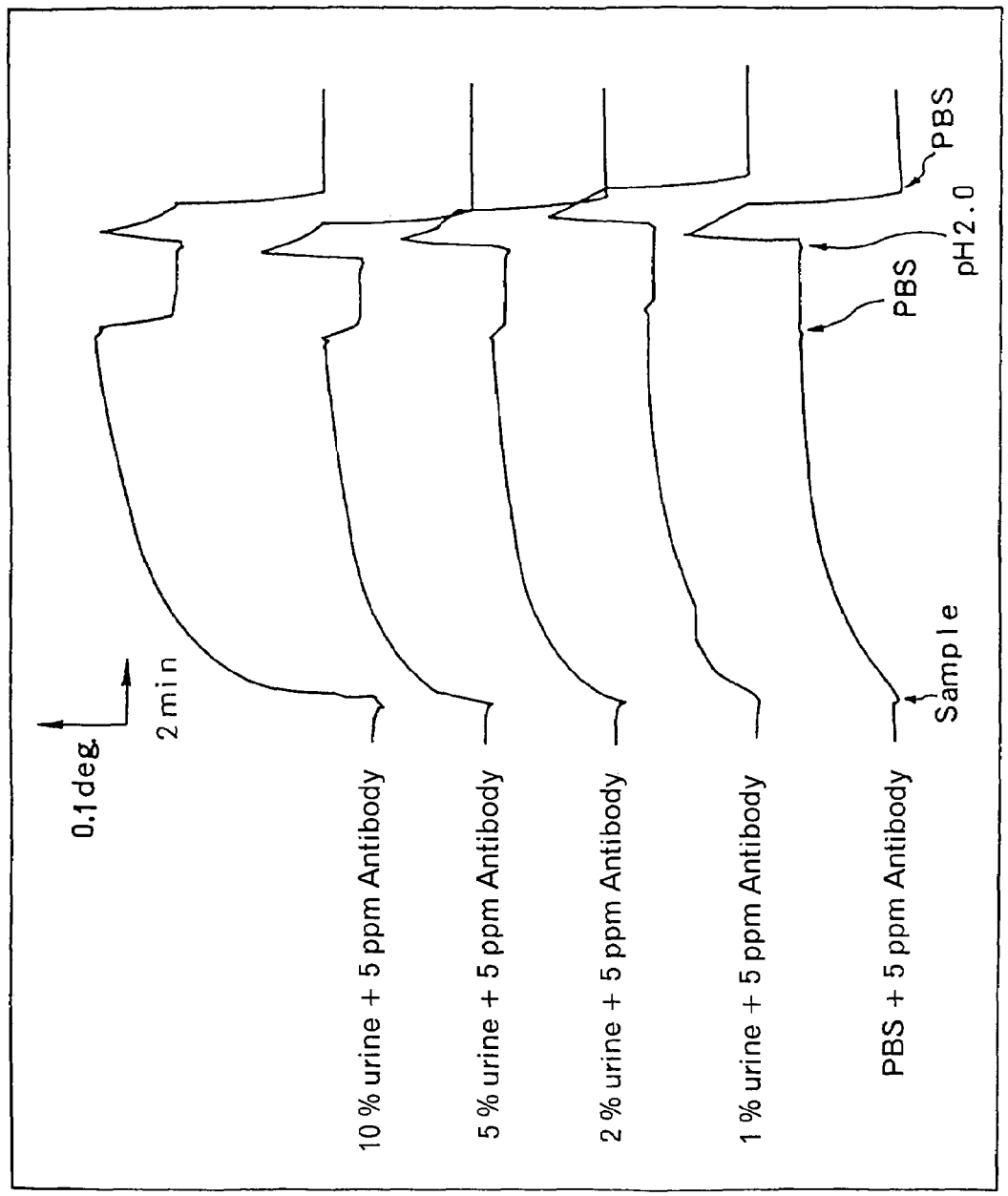
FIG. 6 is a graph depicting response curves of the resonance angles when mixtures each having antibody with a constant concentration of 5 ppm and urine with different concentrations are introduced into the apparatus.
Figure 7:
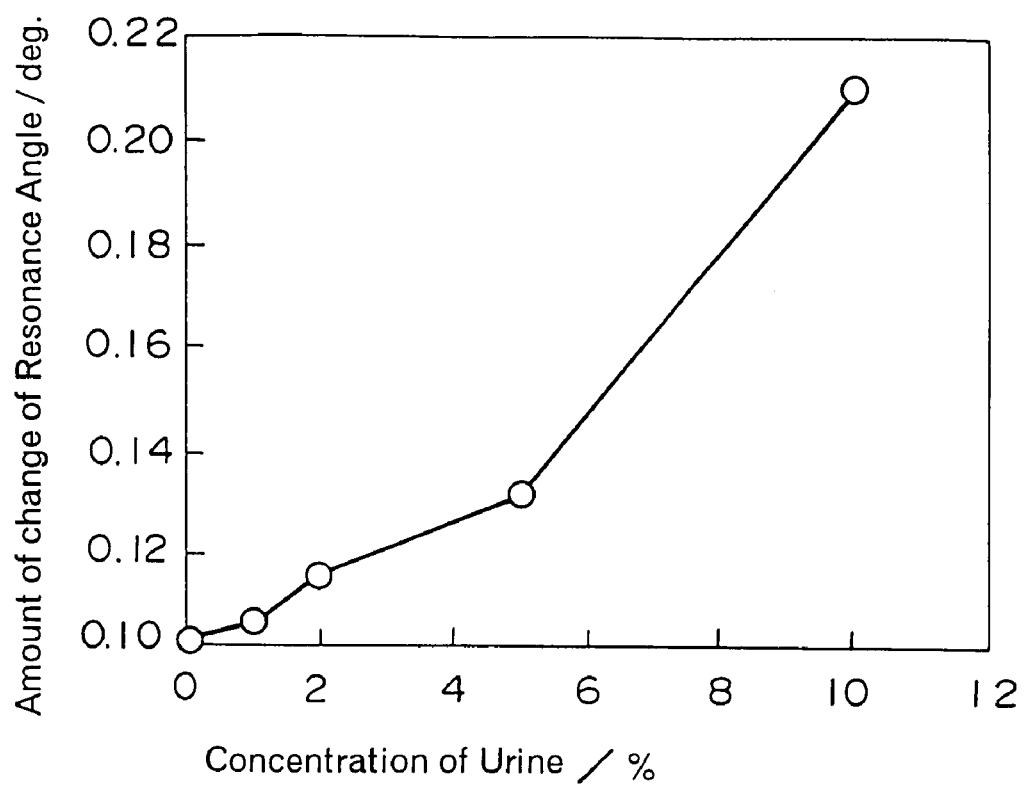
FIG. 7 is a graph illustrating a dependency response upon the concentration of urine when mixtures each having antibody with a constant concentration of 5 ppm and urine with different concentrations are introduced into the apparatus.

FIG. 6 is a graph representing the response curves when 1 ml of antibody solution each containing urine with different concentration is introduced in the flow cell. In FIG. 6, time is taken on the horizontal axis and the resonance angle is taken on the vertical axis; and the mark "sample" indicated by an arrow shows a time when each solution containing urine (sample) starts to be introduced into the cell. Further, FIG. 7 is a graph illustrating a dependency to the concentration of urine in the response of the resonance angle, where the amount of the change of the resonance angle is taken on the vertical axis and the concentration of the antibody is on the horizontal angle. In FIG. 7, differences between the first resonance angle (1) before the samples are introduced into the cell and the second resonance angle (2) after the antigen-antibody reaction has been finished and the response has been stabilized are plotted.

According to FIG. 6, when the concentration of the urine contained into the antibody solution to be introduced in the flow cell is 10%, two times or more higher response was obtained in comparison to the case of the antibody solution which does not contain urine. The reason why is considered such that the protein contained in urine adheres to the antibody in a non specific manner. While, it is also recognized that if the urine is diluted to 100 times (1%), the influence from the non specific adhering is reduced.

Relation Between the Concentration of Morphine and the Amount of the Change of the Resonance Angle when Urine Having a Concentration of 1% is Mixed Mixtures in which a certain amount of antibody (5 ppm) and morphine have been preliminarily reacted together are introduced in the flow cell using a buffer solution which is obtained by diluting urine to 100 times by PBS, and circulated at a room temperature to study the relation between the concentration of morphine and the amount of the change of the resonance angle under the condition that urine exists.

The mixtures, which contain urine, including the antibody solution having a concentration of 5 ppm and morphine having different concentrations in a range of 1 to 10 ppb were obtained in such a manner that 3 µl of the raw liquid material of antibody with a concentration of 1700 ppm and a certain amount of morphine, and the buffer solution, i.e. urine diluted to 100 times by PBS are mixed together, so as to have 1 ml of samples each having a different concentration of morphine, and reacted for 10 minutes at a room temperature.

Figure 8:
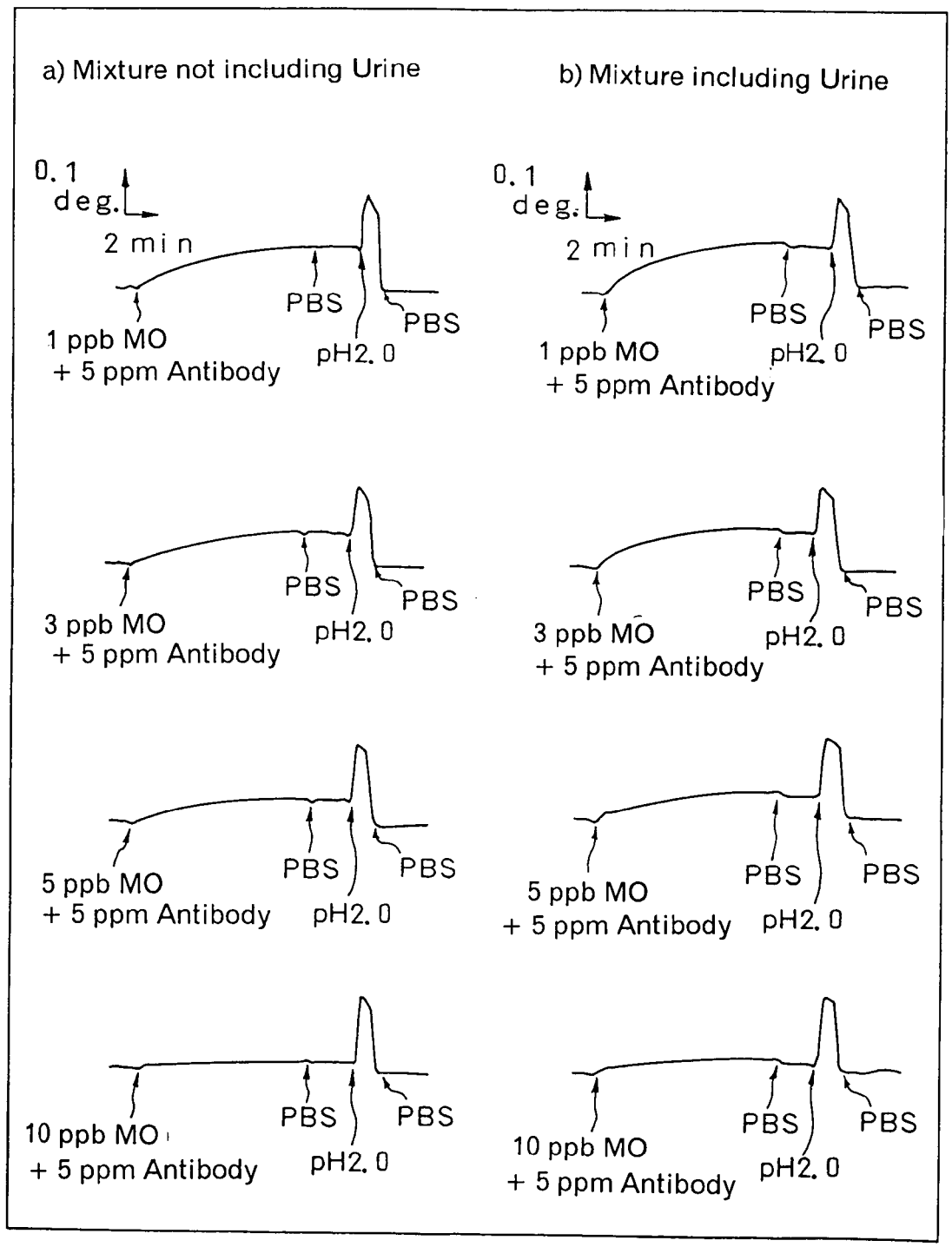
FIG. 8 shows two series of graphs representing response curves of the resonance angles; one of which is obtained when mixtures, which contain 1% of urine, each having antibody with a constant concentration of 5 ppm and morphine with different concentrations are introduced into the apparatus; and the other one of which is obtained when mixtures, which do not contain urine, each having antibody with a constant concentration of 5 ppm and morphine with different concentrations are introduced into the apparatus.
Figure 9:
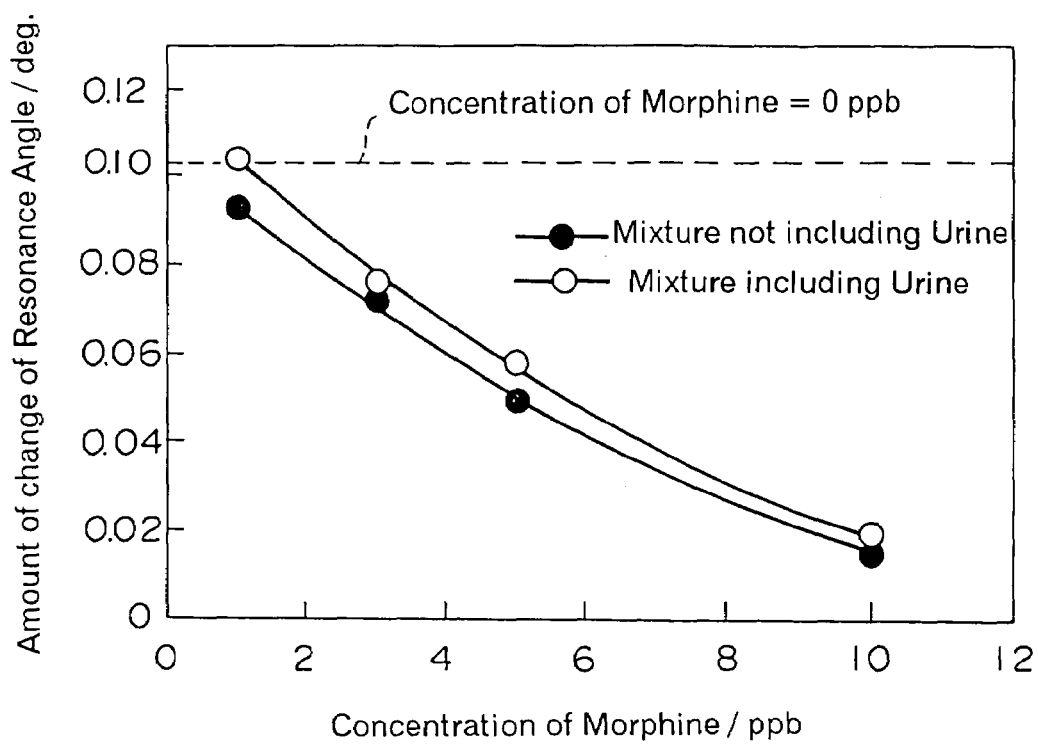
FIG. 9 is a graph representing dependency responses upon the concentration of morphine; one of which is obtained when mixtures, which contain 1% of urine, each having antibody with a constant concentration of 5 ppm and morphine with different concentrations are introduced into the apparatus; and the other one of which is obtained when mixtures, which do not contain urine, each having antibody with a constant concentration of 5 ppm and morphine with different concentrations are introduced into the apparatus.

FIG. 8 is a graph representing the response curves when 1 ml of mixture containing urine (b) and 1 ml of the mixture but containing no urine (a). In FIG. 8, time is taken on the horizontal axis and the resonance angle is taken on the vertical axis; and the indication shown by an arrow with the concentrations of morphine and antibody means a time when each mixture (sample) starts to be introduced in the cell. Further, FIG. 9 is a graph illustrating a dependency to the concentration of morphine in the response of the resonance angle, where the amount of the change of the resonance angle is taken on the vertical axis and the concentration of the antibody is on the horizontal angle. In FIG. 9, differences between the first resonance angle (1) before the sample is introduced and the second resonance angle (2) after the antigen-antibody reaction has been finished and the response has been stabilized are plotted.

According to the result shown in FIG. 9, when the concentration of the urine contained into the antibody solution to be introduced in the flow cell is 1%, the reaction was greater by about 10% in comparison to the case of the mixture which does not contain urine; in the range of the concentration of morphine of 1 to 10 ppb, a good response can be obtained in accordance with the concentration of the morphine. Generally, since the urine of people, who usually use morphine, contains morphine with a concentration of about 1 ppm, even if the urine is diluted to 1%, it can be expected to detect the morphine having a concentration of about 10 ppb, so that such a diluted urine can be sufficiently put to practical use.

Regeneration of the Sensor

In FIGS. 2, 4, 6 and 8, the marks "PBS", "pH2.0" and "PBS" shown by arrows mean that after the second resonance angles (2) are measured, "PBS", "0.1M glycine+0.1M NaCl+0.1M HCl" and "PBS" are introduced into the flow cell instead of the sample each position (time) and then circulated at a room temperature. By introducing acid material into the flow cell in this manner, it can be recognized that the specific coupling between the antigen and antibody is dissociated from each other so that the value of the resonance angle returns to the value before the sample is introduced into the flow cell. In other words, the sensor can be regenerated.

Figure 10:
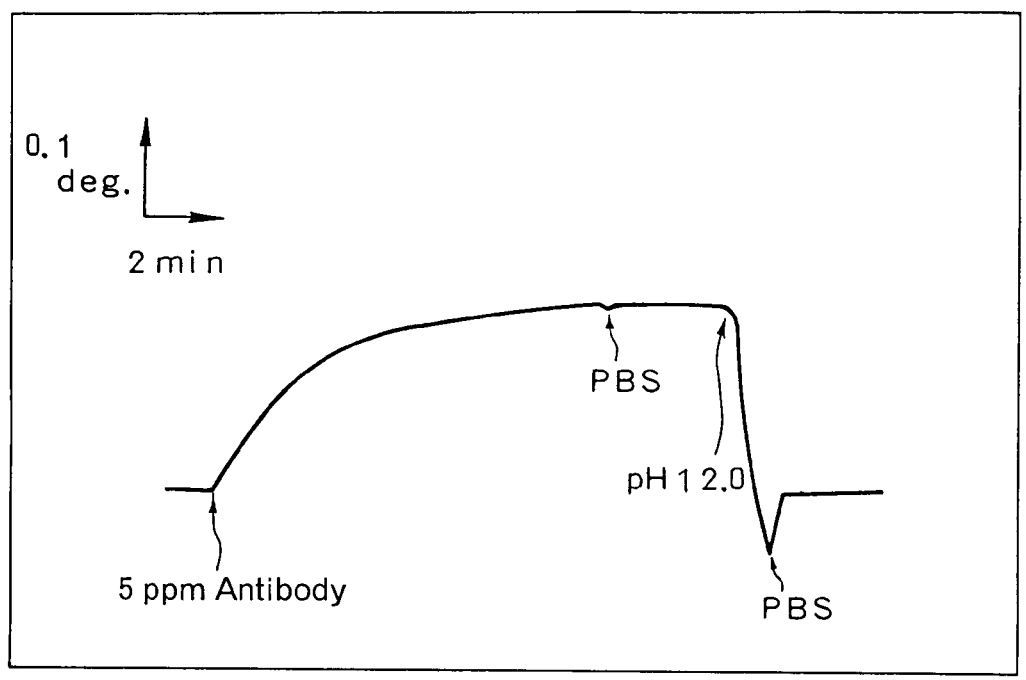
FIG. 10 is a graph depicting a condition for regenerating the sensor where alkali liquid is used.

While, by introducing not only acid material but also alkali material, the sensor can also be regenerated. In FIG. 10, the response of the resonance angle is illustrated after antibody solution containing morphine having a concentration of 5 ppm is introduced into the flow cell and circulated at a room temperature, "PBS", "0.1M glycine+0.1M NaCl+0.1M NaCl" and "PBS" are introduced into the flow cell, and circulated at a room temperature. As clear from FIG. 10, the resonance angle also returns to the value before the sample is introduced into the flow cell by introducing alkali material.

(2) Embodiment 2

Configuration of the Measuring Apparatus

The same apparatus as that of the first embodiment was used.

Preparation of the Sensing Element

The sensing element is completed in such a manner that a thin Gold film is formed on a cover glass (manufactured by Matsunami Glass Co., Ltd.) by a vapor evaporation; then morphine is fixed to the surface of the film.

① Synthesis of N-(4-phthalimidebutyl) Methamphetamine

After melting 1.55 g of methanphetamine 64 ml of dimethylholmamide, 4.39 g of N-(4-bromobutyle) phethalimide and 1.31 g of sodium hydrogencarbonate are added; and then refluxed for 2 hours. After extracting a material from the reacted material with the aide of ethyl acetate, the extracted material is washed by saturated salted water; subjected to a dehydration with the aid of anhydrous sodium sulfate; a solvent medium is evaporated under a reduced pressure to obtain a residue having a black color and a viscosity. The thus obtained residue is refined by silica gel column (Wakogel C-200, 500 ml, developing solvent ethyl acetate→ ethyl acetate:methanol=9:1). The fraction which shows only the spot of $R_f$=0.60 is dispensed by TLC (developing solvent ethyl acetate:methanol=5:1); then the solvent is removed under a reduced pressure to obtain 3.00 g of the objected material. Whether the thus obtained material is an objected N-(4-phthalimidebutyl) methamphetamine is checked by a mass spectroscopy(MS).

② Synthesis of N-(4-aminobutyl) Methamphetamine

Hydrazinolusis of N-(4-phthalimidebutyl) methamphetamine was conducted as in the following, where allyl alcohol is added in the reaction system in order to reduce a side reaction, referring the method by Rice et al.

Into 944 mg of N-(4-phthalimidebutyl) methamphetamine, 2.2 ml of allyl alcohol and 7.9 ml of 90% hydrazine hydrate are added; then is refluxed for one hour in a nitrogen atmosphere. The solvent is removed from the reacted material under a reduced pressure; and the thus obtained residue is refined by silica gel (Wakogel C-200) column (developing solvent chloroform:methanol:water:=10:10:1) The fraction which shows only the spot of $R_f$=0.25 is dispensed by TLC (developing solvent chloroform:methanol:water:=10:10:1); then the solvent is evaporated under a reduced pressure to obtain 397 mg of the desired material. Whether the thus obtained material is the desired N-(4-aminobutyl) methamphetamine is checked by mass spectroscopy(MS).

③ Synthesis of Conjugate (MO-BSA) of N-(4-aminobutyl) methamphetamine and Bovine Serum Albumin (BSA)

Into 0.3 ml of dimethylformamide, is melted 9.7 mg of N-(4-aminobutyl) methamphetamine; then the thus obtained material is further mixed with BSA solution (10 mg/1.5 ml). Into the mixed material, 0.5 ml of 10% solution of 1-ethyle-3-(3-dimethylaminopropyl) carbodiimide hydrochloric acid salt (EDC) is added; the pH thereof is adjusted to 5.5: and then stirred for 16 hours at a room temperature. The thus obtained material is subjected to a dialysis for super pure water, and then frozen and dried up to obtain 10 mg of synthesized material of N-(4-aminobutyl) methamphetamine and bovine serum albumin (MO-BSA:10 mg)

④ Fixing the MA-BSA to the Thin Metal Film

Into the flow cell 6, circulated MA-BSA having a concentration of 100 ppm at a room temperature until the resonance angle becomes constant, i.e. for 3 to 5 minutes, to adhere the MA-BSA on the thin metal film. Then, MA-BSA having a concentration of 1000 ppm is circulated into the flow cell until the resonance angle becomes constant, i.e. for 3 to 5 minutes, under a room temperature to conduct a blocking so that the MO-BSA is not physically adsorbed on the film any more.

Relation Between the Concentration of Methamphetamine and the Amount of the Change of the Resonance Angle Next, mixtures which are obtained by preliminarily reacting a certain amount of antibody having a concentration of 5 ppm and methamphetamine (MA) are introduced into the flow cell 6 and circulated at a room temperature to study the relation between the concentration of methamphetamine and the amount of the change of the resonance angle.

Mixtures containing the antibody and methamphetamine each having a different concentration of methamphetamine in a range of 0.1 to 100 ppm were prepared in such a manner that that 3 μl of the raw liquid material of antibody having a concentration of 1700 ppm mentioned above and 1 ml of mixtures of methamphetamine and PBS each having a different concentration of methamphetamine are mixed together and reacted for about 5 minutes at a room temperature.

Figure 11:
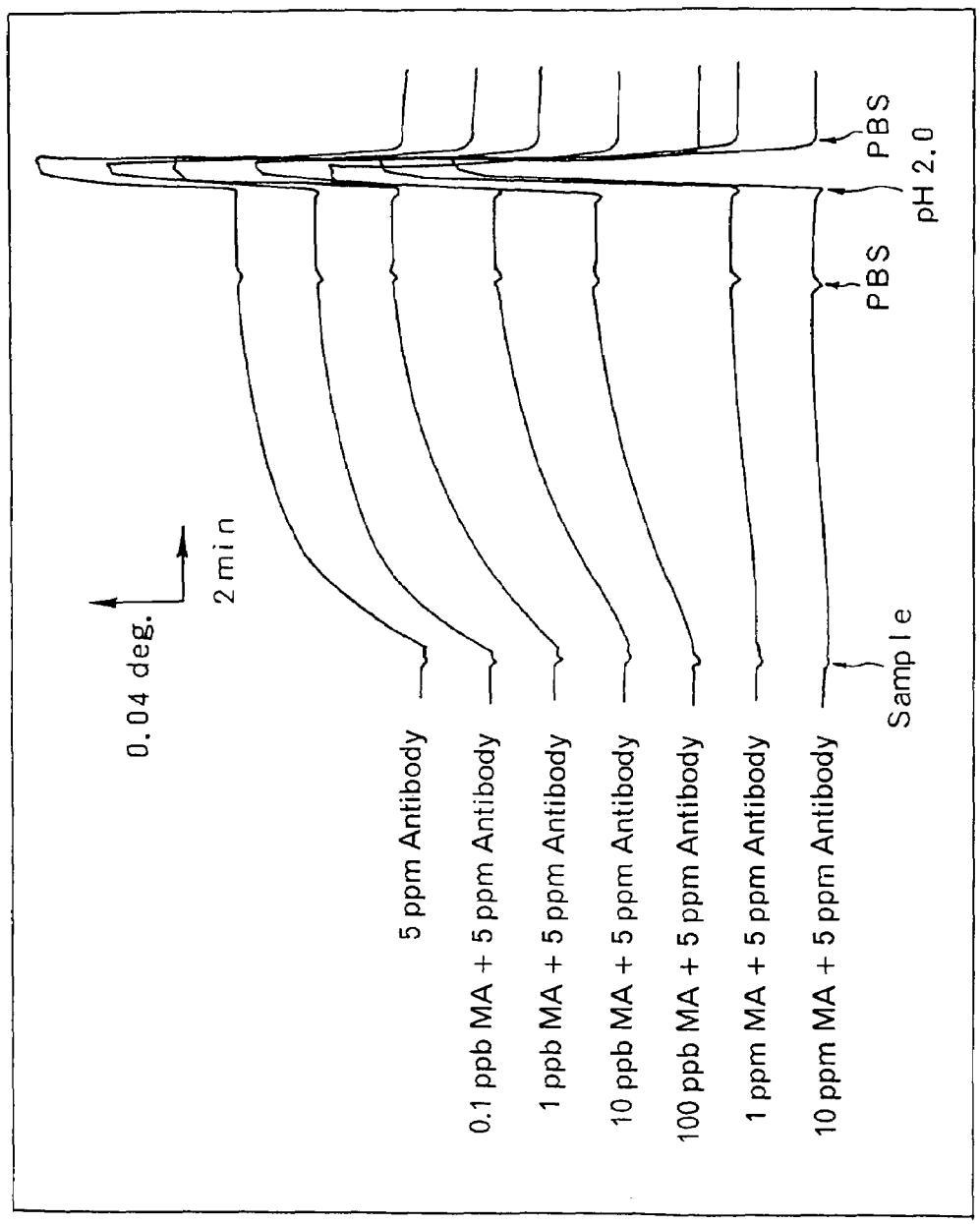
FIG. 11 is a graph illustrating response curves of the resonance angles when mixtures each having antibody with a constant concentration of 5 ppm and methamphetamine with different concentrations are introduced into the apparatus.
Figure 12:
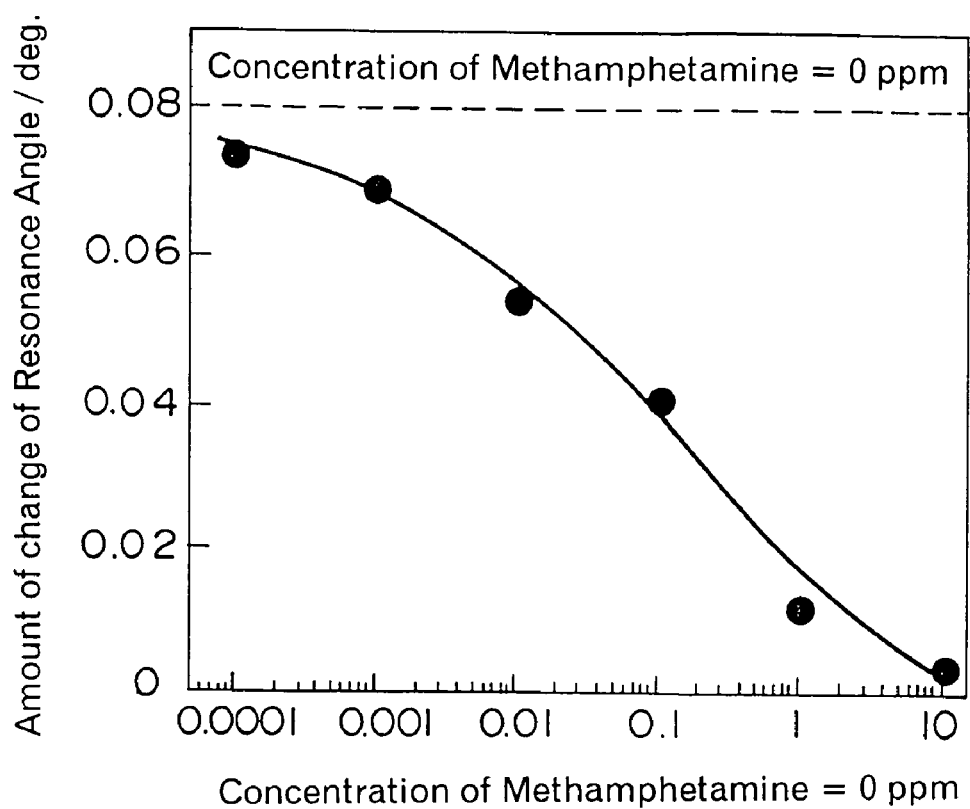
FIG. 12 is a graph representing a dependency response upon the concentration of methamphetamine when mixtures each having antibody with a constant concentration of 5 ppm and methamphetamine with different concentrations are introduced into the apparatus.

FIG. 11 is a graph depicting response curves when each mixture and 1 ml of the antibody solvent including no methamphetamine are introduced in the flow cell. In FIG. 11, time is taken on the horizontal axis and the resonance angle is taken on the vertical axis; and the mark "sample" indicated by an arrow shows a time when each mixture and the solvent including no methamphetamine start to be introduced into the cell. Further, FIG. 12 is a graph illustrating a dependency to the concentration of methamphetamine in response of the resonance angle, where the amount of the change of the resonance angle is taken on the vertical axis and the concentration of the antibody is on the horizontal axis. In FIG. 12, differences between the first resonance angle (1) before the samples are introduced and the second resonance angle (2) after the antigen-antibody reaction has been finished and the response has been stabilized are plotted.

It is recognized that a sufficient change of the resonance angle can be obtained in accordance with the concentration of the methamphetamine contained in the mixture which is introduced in the flow cell.

In the second embodiment, after the second resonance angle (2) are measured, "PBS", "0.1M glycine+0.1M NaCl+

0.1M HCl" and "PBS" are introduced into the flow cell instead of the sample and circulated at a room temperature. By introducing acid material into the flow cell in this manner, it can be recognized that the specific coupling between the antigen and antibody is dissociated from each other so that the value of the resonance angle returns to the value before the sample is introduced into the flow cell. In other words, the sensor can be regenerated even in measuring the methamphetamine by not only introducing the acid into the cell but also alkali.

As explained above, according to the invention, since the medical substance is detected by using a resonance phenomenon with evanescent wave, such as surface plasmon resonance phenomenon, the measurement accuracy is not affected by the coloring of the sample or non-transparency of the sample. Further, the measurement can be conducted with only a small amount of sample in a short time period.

Furthermore, according to the present invention, the change of the condition for generating the resonance based on the coupling of the antibody which has a great molecular weight to the sensor is obtained, and the concentration of the medical substance, which is antigen, is obtained from the change of the condition for generating resonance in an indirect manner. Therefore, even if the medical substance to be measured has only a small molecular weight, it is possible to detect it with a high accuracy.

Furthermore, in case the antibody has been preliminarily fixed on the resonance material such as a thin metal film, etc., there is a disadvantage that the activity of immunity of the antibody is decreased due to the change of the construction of the antibody when the antibody is fixed or due to the change of the antibody when a long time has passed after the antibody was fixed, so that the measurement accuracy becomes low. However, according to the invention, since the antigen as an object to be measured is fixed to the thin metal film, the disadvantage is solved that the activity of the immunity of the antibody is decreased.

Moreover, according to the invention, the pre-treatment for the measurement is very simple which is only to adjust a mixture of the sample liquid and antibody.

What is claimed is:

1. An apparatus for measuring a medical substance (an antigen) contained in a sample using a resonance phenomenon resonating with an evanescent wave, said apparatus, comprising:
   a resonance phenomenon generating section having a resonance material; and
   a detecting means for detecting a change of an incident light which is made incident upon said resonance material to generate said resonance phenomenon or a change of a reflected light thereof
   wherein the medical substance (antigen) to be measured is fixed to said resonance material.

2. An apparatus according to claim 1, wherein said change to be detected by said detecting means is an incident angle of said light being made incident upon said resonance material when an intensity of the reflected light thereof is decreased.

3. An apparatus according to claim 1, wherein said change to be detected by said detecting means is a wavelength or a wave number of said reflected light when an intensity of said reflected light is decreased.

4. An apparatus according to claim 3, wherein said resonance phenomenon is a surface plasmon resonance phenomenon.

5. An apparatus according to claim 1, wherein said change to be detected by said detecting means is an intensity of said reflected light when the incident light is made incident upon said resonance material with a predetermined incident angle.

6. An apparatus according to claim 5, wherein said resonance phenomenon is a surface plasmon resonance phenomenon.

7. An apparatus according to claim 1, wherein said change to be detected by said detecting means is an incident angle of said incident light when a phase of said reflected light is varied.

8. An apparatus according to claim 1, wherein said resonance phenomenon is a surface plasmon resonance phenomenon.

9. An apparatus according to claim 8, wherein said resonance phenomenon generating section comprises a prism having a high refractive index, a thin metal film directly or indirectly formed on one of the surfaces of said prism as said resonance material, and a light source for making a light incident upon said metal film via said prism, wherein the medical substance (antigen) to be measured is fixed to a surface of said metal film.

10. An apparatus according to claim 9 further comprising a calculating means for recognizing an amount of said medical substance (antigen) contained in said sample in accordance with the change detected by said detecting means.

11. A medical substance sensor for use in an apparatus for measuring a medical substance (an antigen) contained in a sample using a resonance phenomenon resonating with an evanescent wave comprising a resonance material where the resonance phenomenon is caused to resonate with an evanescent wave, wherein the medical substance (antigen) to be measured is fixed to said resonance material.

12. A medical substance sensor according to claim 11 further comprising a prism having a high refractive index, a thin metal film which is directly or indirectly formed on one of the surfaces of said prism as said resonance material, wherein the medical substance (antigen) to be measured is fixed to a surface of said metal film.

* * * * *